United States Patent [19]
Islam

[11] Patent Number: 5,203,866
[45] Date of Patent: Apr. 20, 1993

[54] STILETTED NEEDLES

[76] Inventor: Abul B. M. A. Islam, 651 Elm St., Apt. 9A, Buffalo, N.Y. 14203

[21] Appl. No.: 697,079

[22] Filed: May 8, 1991

[30] Foreign Application Priority Data

May 9, 1990 [GB] United Kingdom ............... 9010427

[51] Int. Cl.⁵ ............................................ A61M 5/178
[52] U.S. Cl. .................... 606/186; 606/185; 604/164; 604/51
[58] Field of Search .............. 606/185, 186, 51, 52, 606/53; 604/51-53

[56] References Cited

U.S. PATENT DOCUMENTS

| | | | |
|---|---|---|---|
| 4,331,138 | 5/1982 | Jessen | 606/185 X |
| 4,485,815 | 12/1984 | Amplatz et al. | 606/185 |
| 4,582,061 | 4/1986 | Fry | 606/185 |
| 4,654,030 | 3/1987 | Moll et al. | 606/185 X |
| 4,940,458 | 7/1990 | Cohn | 604/51 |
| 5,030,206 | 7/1991 | Lander | 606/185 X |

FOREIGN PATENT DOCUMENTS 108491 5/1964 Netherlands .................. 606/185

Primary Examiner—Peter A. Aschenbrenner
Attorney, Agent, or Firm—Trexler, Bushnell, Giangiorgi & Blackstone, Ltd.

[57] ABSTRACT

The invention relates to stiletted needles and has for its object to enable the removal of a stilette from the needle once the needle is inserted into a patient, with the elimination of jarring of the needle. This objective is met by a construction comprising a body member, a needle extending from the body member, with a bore of the body member co-axial with the bore of the needle, a stilette, extending from a hand grip for the stilette, there being pin means on the hand grip to engage slot means in the end of the body member, said slot means having at least one side wall forming a cam surface for engagement by the pin means.

4 Claims, 1 Drawing Sheet

STILETTED NEEDLES

This invention relates to stiletted needles such as are used in many applications where a hollow needle must be blocked during insertion into the body of a patient, and unblocked to enable the needle to serve its intended function.

One such use is in sternal puncture as is extensively used in the investigation and diagnosis of various blood dyscrasias, and where the needle must be blocked such as by a stilette whilst the needle is forced through the sternum and to prevent the needle from being blocked by skin, subcutaneous tissue or bone fragments, and the stilette then removed to allow the extraction of a bone marrow aspirate sample. A secondary but important function of the stilette is to provide added strength to the needle during its insertion and extraction.

Because the needle must have a sharp point, it is known to bevel the tip of the needle, and because the needle must be blocked to the tip, it is known to similarly bevel the tip of the stillette necessitating the provision of means to ensure correct alignment of the bevels on the needle and the stilette.

Thus, with conventional sternal puncture needles a body member generally of cylindrical configuration is provided and to which the needle is attached, the stilette extending from a boss on the gripping head, the boss being of conical configuration to locate in a correspondingly conical bore in the body member. With the stilette passed down the needle, the boss on the gripping head engages in the bore of the cylindrical body member, and to ensure alignment of the bevels on the needle and the stilette, a pin on the head slidably engages in a slot in the end of the body member. An adjustable guard can be secured at an appropriate point along the length of the needle to prevent overpenetration, but more usually it is the finger of an operative laid along the needle that is used to sense that required penetration has been achieved.

Conventional sternal puncture needles are not comfortable to use, being short and not fitting properly in the users hands. The pressure applied to insert the needle causes a tight fit between the boss bearing the stilette and the bore in the body member. Once inserted, removal of the stilette is by gripping and pulling the head to free the pin from the groove, an action that can jar the needle. Such needles have been the subject of a notable recent improvement, where the body member is formed of T-shape and the head of the stilette formed as an enlarged shallow dome. This allows the needle to fit most comfortably in the hand of the user with greater control and feel over the pressure applied to bring about penetration. However a corresponding conical boss on which the stilette is provided and bore in the body member has been retained, with the problem of jarring of the needle as the stilette is removed.

The object of the invention is to provide an improved form of stiletted needle.

According to the present invention, a stiletted needle comprises a body member, a needle extending from the body member, with a bore of the body member co-axial with the bore of the needle, a stilette, extending from a hand grip for the stilette, there being pin means on the hand grip to engage slot means in the end of the body member, said slot means having at least one side wall forming a cam surface for engagement by the pin means.

Preferably, the body member is of T-shape and the hand grip of the stilette of enlarged dome form, with a boss bearing the pin means, and from which the stilette extends.

Thus, the stiletted needle of the invention has the convenience and comfort of use as is mentioned above, but after insertion of the needle, the need to pull the stilette from the needle is eliminated. After insertion, the hand grip is simply rotated to bring the pin against the cam surface of the slot, and when the pin rides up the surface to allow the extraction of the stilette in the complete absence of any jaring of the inserted needle.

With the known form of construction with a shallow dome on the stilette, its centre of gravity is such that the head can hold the stilette in an upright position, a dangerous disposition to the user. A further feature of the invention is to provide a head of semicircular cross-section, retaining comfort of fit in the hand of the user, but ensuring that the stilette will always be point down on a surface when clear of the needle.

Whilst conventional bevelling of tip of the needle generates a relatively sharp point, sharpness is noticably improved in accordance with a still further feature of the invention, where the bevelled tip of the needle is formed, such as by grinding, with two flat side faces, extending from the tip of the bevel and part way along the bevel.

In addition to being formed with its cam-faced slot, the end of the housing is also formed such that it can readily be attached to, for example, a syringe for the extraction of bone marrow, blood or other fluid material required to be extracted. Equally the end of the housing can be formed for ready attachment to supply means for fluid substances to be fed into the body of the patient.

One embodiment of the invention will now be described with reference to the accompanying drawings in which.

Figure 1:
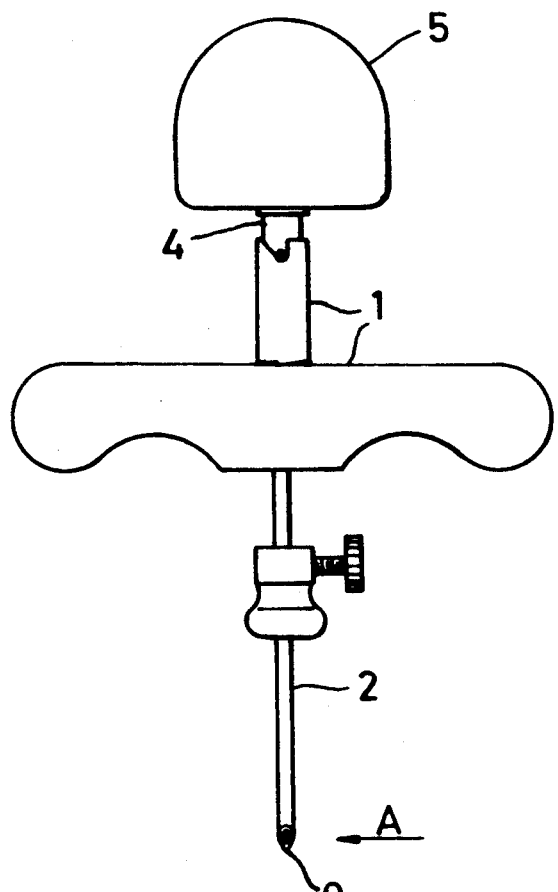
FIG. 1 is a side elevation of a stiletted needle in accordance with the invention.
Figure 2:
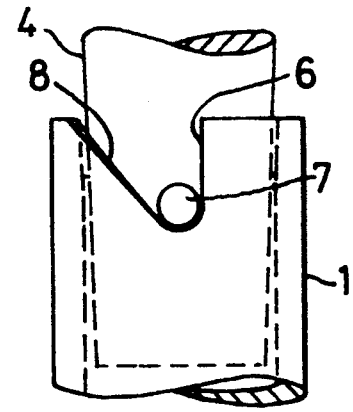
FIG. 2 is an enlarged view of the part of the body member of FIG. 1, bearing the cam surface.

In the drawings, a stiletted needle has a body member 1 of generally T-shape, from which extends a needle 2, the needle having a longitudinal bore co-axial with a bore through the body member. The bore through the needle is of a diameter such that a stilette 3 is a close sliding fit therethrough, and the bore through the body member of enlarged diameter to receive a boss 4 on a domed head 5 of the stilette 3, the boss 4 and the outer end of the bore through the body member being correspondingly conically tapered.

In the end of the body member, a slot 6 is formed into which a pin 7 on the boss 4 of the stilette can engage, one side wall 8 of the slot being formed as a cam surface.

The needle 2 and the stilette 3 are correspondingly bevelled at 9 and 11 to generate a sharp point, and with the stilette inserted in the needle and with the pin 7 engaging the slot 6, the needle and the stilette are co-terminus and with their respective bevels in alignment, and with the conical boss 4 in firm engagement in the correspondingly conical end of the bore in the T-shaped body.

Thus the T-shaped body and the domed head on the stilette combine to provide convenience of use and comfort to the user, to the benefit of the user in introducing the needle into the body of a patient, with the degree of penetration, if required, being limited by an adjustable guard 10 that can be strategically located along the length of the needle.

Once the needle is inserted into a patient, the domed head 5 of the stilette can be gripped and rotated, to urge the pin 7 on the boss 4 against the cam surface 8 of the slot in the end of the body member, and when the pin rides up the cam surface to disengage the conical boss 4 from the end of the bore in the body member in the complete absence of any jarring of the inserted needle.

Thus, with the stilette inserted in the needle, introducing the needle into a patients body is effected with the prevention of any material penetrating and blocking the bore in the needle, and with the stilette removed, a syringe for the extraction of material from the patient can be suitably attached to the body member, and equally means for the supply of a required substance into the patient can suitably be attached to the body member.

Figure 3:
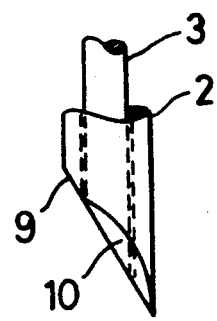
FIG. 3 is an enlarged view of the tip of the needle of FIG. 1, extending from the body member.
Figure 4:
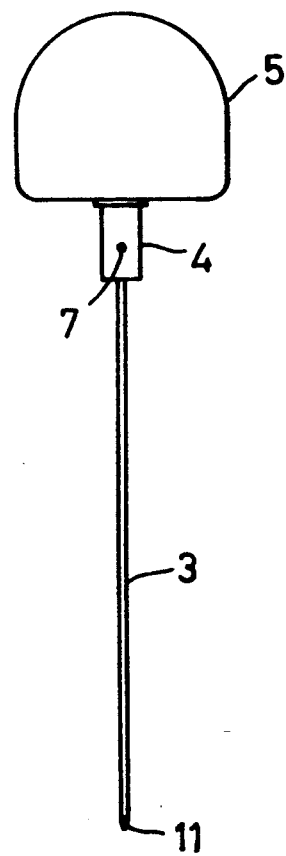
FIG. 4 is a side elevation of the stilette of the stiletted needle of FIG. 1.

Whilst conventional bevelling of the tip of the needle generates a reasonably sharp point, sharpness is greatly enhanced by the additional grinding of two flat faces 10 to the sides of the bevel as is illustrated in FIG. 3.

A further advantage of the construction of the drawings is the provision of a domed head 5 of semi-circular cross-section. Here, and unlike the prior art, with the stilette removed from the needle, it is impossible for the stilette to assume a vertical position when resting on the boss, placing the stilette on a tray or the like inevitably resulting in the stilette lying point downwards against the tray or the like.

I claim:

1. A stiletted needle comprising a body member, a needle extending from the body member, with a bore of the body member co-axial with a bore of the needle, a stilette extending from a hand grip for the stilette, and being removably extendable through said needle bore, there being pin means on the hand grip to engage slot means in the end of the body member, said slot means having at least one side wall forming a cam surface for engagement and rotation of the pin means and stylette as the stylette is moved in the bore of the needle, the hand grip of the stilette being of semi-circular cross-section.

2. A stiletted needle comprising a body member, a needle extending from the body member, with a bore of the body member co-axial with a bore of the needle, a stilette extending from a hand grip for the stilette, and being removably extendable through said needle bore, there being pin means on the hand grip to engage slot means in the end of the body member, said slot means having at least one side wall forming a cam surface for engagement by the pin means, and wherein in addition to conventional bevelling at the tip of the needle, the bevelled tip is formed with two flat side faces extending from the tip of the bevel and along the bevel to each side.

3. A stiletted needle as in claim 1, wherein the body member is of T-shape and the hand grip of the stilette of enlarged dome form, with a boss bearing the pin means, and from which the stilette extends.

4. A stiletted needle as in claim 3, wherein the boss and the end of the bore of the body member are correspondingly tapered.

* * * * *